United States Patent [19]

Furlan

[11] Patent Number: 5,120,851

[45] Date of Patent: Jun. 9, 1992

[54] PREPARATION PROCESS FOR MAKING WATER-SOLUBLE LYSINE SALTS OF (+)2-(4-FLUOROPHENYL)-ALPHA-METHYL-5-BENZOXAZOLE ACETIC ACID

[75] Inventor: Diego Furlan, Segrate, Italy

[73] Assignee: Euroresearch S.r.l., Milan, Italy

[21] Appl. No.: 437,664

[22] Filed: Nov. 17, 1989

Related U.S. Application Data

[62] Division of Ser. No. 293,668, Jan. 5, 1989, Pat. No. 4,897,408.

[30] Foreign Application Priority Data

Jan. 13, 1988 [IT] Italy ............... 19057 A/88

[51] Int. Cl.⁵ ........................................... C07D 263/56
[52] U.S. Cl. ................................................ 548/217
[58] Field of Search ...................... 548/217; 562/562

[56] References Cited

U.S. PATENT DOCUMENTS

| | | | |
|---|---|---|---|
| 3,598,838 | 8/1971 | Toj et al. | 562/562 |
| 3,912,748 | 10/1975 | Evans | 548/217 |
| 3,988,466 | 10/1976 | Takagi et al. | 514/564 |
| 4,420,432 | 12/1983 | Chibata et al. | 562/562 |
| 4,434,163 | 2/1984 | Lombardino | 514/226.5 |
| 4,652,654 | 3/1987 | Verga et al. | 548/217 |
| 4,699,927 | 10/1987 | De Boeck | 562/562 |
| 4,748,174 | 5/1988 | Veronesi | 514/411 |
| 4,749,694 | 7/1988 | Fix et al. | 514/203 |
| 4,797,423 | 10/1989 | Benant | 514/555 |

FOREIGN PATENT DOCUMENTS 1080779  5/1985  Italy.

OTHER PUBLICATIONS

Chem. Abstr. Vol. 82, Entry 118774b, 1975.

*Primary Examiner*—Donald G. Daus
*Attorney, Agent, or Firm*—Parkhurst, Wendel & Rossi

[57] ABSTRACT

Water-soluble salts of (+)2-(4-fluorophenyl)-alpha-methyl-5-benzoxazole acetic acid with DL-lysine, D-lysine or L-lysine, suitable for the preparation of medicinal specialities such as syrups, creams, suppositories, aqueous solutions for personal hygiene etc, and their preparation process.

The salts are obtained by suspending said acid in an organic solvent soluble or partly soluble in water, adding an equivalent quantity of the lysine and crystallizing the salt obtained.

2 Claims, No Drawings

PREPARATION PROCESS FOR MAKING WATER-SOLUBLE LYSINE SALTS OF (+)2-(4-FLUOROPHENYL)-ALPHA-METHYL-5-BENZOXAZOLE ACETIC ACID

This is a division of application Ser. No. 07/293,668 filed Jan. 5, 1989, U.S. Pat. No. 4,897,408.

FIELD OF THE INVENTION

This invention relates to water-soluble salts of (+)2-(4-fluorophenyl)-alpha-methyl-5-benzoxazole acetic acid, hereinafter also called flunoxaprofen, which are suitable for the preparation of medicinal specialities such as syrups, creams, suppositories, aqueous solutions for personal hygiene etc, possessing antiinflammatory, analgesic and antipyretic activity, and to their preparation process.

PRIOR ART (+)2-(4-fluorophenyl)-alpha-methyl-5-benzoxazole acetic acid is known both in its raceme form and in its dextrorotatory and levorotatory forms. It is also known to possess considerable anti-inflammatory, analgesic and antipyretic activity (J. Medic. Chem. 1975, vol 18, No. 1, pp 53-58). The dextrorotatory form is particularly active, demonstrating a much higher therapeutic index than known very active anti-inflammatories such as indomethacin and diclofenac (Italian patent No. 1,080,779).

However, because of its very limited water-solubility, flunoxaprofen encounters extremely serious limitations in the preparation of certain medicinal specialities such as syrups, creams, suppositories, aqueous solutions for personal hygiene, etc.

There is therefore a much-felt need for flunoxaprofen in water-soluble form.

SUMMARY OF THE INVENTION

We have now found that water-soluble salts of flunoxaprofen are obtained by salifying it with lysine, which can be used in raceme, dextrorotatory or levorotatory form.

The object of the present invention is therefore to provide flunoxaprofen salts with lysine in raceme, dextrorotatory or levorotatory form.

A further object of the present invention is to provide a process for preparing said salts, consisting of suspending the flunoxaprofen in an organic solvent soluble or partly soluble in water, quickly adding an equivalent quantity of lysine and crystallizing the salt obtained by cooling.

DETAILED DESCRIPTION OF THE INVENTION

To prepare the salts of the present invention, the flunoxaprofen is suspended in an organic solvent soluble or partly soluble in water, in a quantity of 200-350 g per 1000 ml of solvent.

The solvent is preferably chosen from the group consisting of $C_1$-$C_4$ alcohols, ketones such as acetone and methylethylketone, ethyl acetate and acetonitrile.

The flunoxaprofen suspension is heated to a temperature of between 20° and 80° C. and an equivalent quantity of lysine in raceme, dextrorotatory or levorotatory form in aqueous solution at a concentration of up to 60% by weight or in solid form with an $H_2O$ content of up to 10% by weight. A clear solution immediately forms. The salt of flunoxaprofen with lysine then precipitates at a temperature of between −5° and +30° C.

The salt is recovered by filtration, washed with the solvent and dried under vacuum at a temperature of between 50° and 70° C.

The salt obtained has a water-solubility at 20° C. of 100 g per 100 ml.

When subjected to pharmacological tests, the obtained salt demonstrates anti-inflammatory properties equal to flunoxaprofen itself, for an equivalent flunoxaprofen concentration.

The $LD_{50}$, $ED_{50}$ and TI (therapeutic index) values are given hereinafter for the salt of flunoxaprofen with DL-lysine compared with flunoxaprofen and diclofenac, which is a well-known very active anti-inflammatory.

The $LD_{50}$ was determined by the Litchfield-Wilcoxon method on mice using progressive oral doses. The $ED_{50}$ was determined by the test involving experimental edema induced by carrageen in a rat's paw (Sprague Dawley—Charles River): in this test the medicament is administered in 3 or 4 different progressive does 60 minutes before inoculating 0.05 ml of a 1% carrageen solution under the plantar aponeurosis. The paw volume is checked 2, 4 and 6 hours after inoculating the carrageen.

The results obtained were as follows:

|  | $LD_{50}$ mg/kg | $ED_{50}$ mg/kg | TI $LD_{50}/ED_{50}$ |
|---|---|---|---|
| Salt of flunoxaprofen with DL-lysine | 720.0 (*) | 5.54 (*) | 129.96 |
| Flunoxaprofen | 723.5 | 5.97 | 121.18 |
| Diclofenac | 235.0 | 10.0 | 23.5 |

(*) expressed as flunoxaprofen

The salts according to the invention may be used for the preparation of pharmaceutical compounds added with common ingredients known in the pharmaceutical technique for obtaining syrups, creams, suppositories, aqueous solutions for person hygiene etc.

The following examples of the preparation of salts according to the invention are given for the purposes of non-limiting illustration.

EXAMPLE 1

285 g of (+)2-(4-fluorophenyl)-alpha-methyl-5-benzoxazole acetic acid are suspended in 1000 ml of isopropyl alcohol. The suspension obtained is heated to 60° C. under stirring and 292 g of a 50 weight % aqueous solution of DL-lysine are then quickly added.

A clear solution is immediately obtained, and precipitation of the salt of (+)2-(4-fluorophenyl)-alpha-methyl-5-benzoxazole acetic acid with DL-lysine commences after a few minutes. The mixture is cooled to 0° C., filtered and the salt washed with isopropyl alcohol. The salt is then dried at 60° C. under vacuum.

428 g of the desired product are obtained with a melting point of 194°-196° C. and a water-solubility at 20° C. of 100 g per 100 ml.

The DL-lysine titre in the obtained salt is 33.8% and the (+)2-(4-fluorophenyl)-alpha-methyl-5-benzoxazole acetic acid titre is 66.1%.

EXAMPLE 2

Example 1 is repeated using 1200 ml of ethyl acetate as solvent, and L-lysine instead of DL-lysine.

425 g of salt are obtained having an L-lysine titre of 33.6% and a (+)2-(4-fluorophenyl)-alpha-methyl-5-benzoxazole acetic acid titre of 66.0%.

The water-solubility is as in Example 1.

EXAMPLE 3

Example 1 is repeated using 1200 ml of acetone as solvent and 146 g of D-lysine as reagent.

426 g of salt are obtained having a D-lysine titre of 33.8% and a (+)2-(4-fluorophenyl)-alpha-methyl-5-benzoxazole acetic acid titre of 66.0%.

The water-solubility is as in Example 1.

I claim:

1. A process for preparing a water-soluble salt of (+)2-(4-fluorophenyl)-alpha-methyl-5-benzoxazole acetic acid with DL-lysine, D-lysine, or L-lysine consisting of:

(a) suspending from about 200 to about 350 g of (+)2-(4-fluorophenyl)-alpha-methyl-5-benzoxazole acetic acid in 1000 ml of a water-soluble or partly water-soluble organic solvent selected from the group consisting of $C_1$–$C_4$ alcohol, acetone, methylethylketone, ethyl acetate and acetonitrile;

(b) stirring the acid suspension of step (a) at a temperature of from about 20° to about 80° C.;

(c) quickly adding to the stirred acid suspension an equivalent amount of DL-lysine, D-lysine, or L-lysine in the form of an aqueous solution having an up to 60% by weight concentration or in solid form with a water content of up to 10% by weight to form a water-soluble salt; and (d) cooling the resulting salt to crystallize it.

2. The process of claim 1, wherein step (d) is carried out at a temperature of from about −20° to about 30° C.

* * * * *